(12) United States Patent
Kim

(10) Patent No.: US 7,186,257 B2
(45) Date of Patent: Mar. 6, 2007

(54) AUXILIARY APPARATUS FOR INSERTING A PIN INTO A BROKEN BONE

(76) Inventor: Jun Hyun Kim, 305-701, Namcheon Samic Beach Apt. Namcheon 2-Dong, Suyeong-ku (KR)

( * ) Notice: Subject to any disclaimer, the term of this patent is extended or adjusted under 35 U.S.C. 154(b) by 322 days.

(21) Appl. No.: 10/865,131

(22) Filed: Jun. 9, 2004

(65) Prior Publication Data
US 2004/0249389 A1    Dec. 9, 2004

(30) Foreign Application Priority Data
Jun. 9, 2003  (KR) .................. 10-2003-0036856
Nov. 13, 2003  (KR) .................. 10-2003-0080056

(51) Int. Cl.
*A61B 17/17* (2006.01)
(52) U.S. Cl. ..................................... 606/96
(58) Field of Classification Search .................. 606/96, 606/80, 86, 98, 99, 104
See application file for complete search history.

(56) References Cited
U.S. PATENT DOCUMENTS

| | | | |
|---|---|---|---|
| 3,867,932 A * | 2/1975 | Huene | 606/80 |
| 3,975,032 A * | 8/1976 | Bent et al. | 279/30 |
| 5,284,483 A * | 2/1994 | Johnson et al. | 606/86 |
| 5,868,750 A * | 2/1999 | Schultz | 606/104 |
| 6,716,215 B1 * | 4/2004 | David et al. | 606/80 |
| 2004/0097947 A1 * | 5/2004 | Wolford et al. | 606/80 |

* cited by examiner

Primary Examiner—Eduardo C. Robert
Assistant Examiner—David Comstock
(74) Attorney, Agent, or Firm—Jordan and Hamburg LLP

(57) ABSTRACT

An auxiliary apparatus for inserting a pin into a broken bone enhances the precision of an orthopedic medical operation. The auxiliary apparatus includes a shaft including a drill chuck part installed at its outer front end, a handle mounting part disposed at its middle portion, and a tool joint part formed at its rear end, in which a pin inserting hole is formed through an inner side of the shaft, a staged portion and a locking groove formed at the handle mounting part, and a cap bolt inserted into the tool joint part. A support handle is rotatably mounted onto the handle mounting part of the shaft. A shaft inserting hole is formed through in the support handle. An engaging hole for receiving a release prevention bolt and a joint groove are formed at a radial outer side of the support handle.

1 Claim, 9 Drawing Sheets

AUXILIARY APPARATUS FOR INSERTING A PIN INTO A BROKEN BONE

BACKGROUND OF THE INVENTION

1. Field of the Invention

The present invention relates to an auxiliary apparatus for inserting a pin into a broken bone, more particularly to an auxiliary apparatus for inserting a pin into a broken bone, which is capable of being easily mounted to a conventional electric-powered drill, in which a support handle is rotatably mounted onto an outer peripheral surface of a hollow shaft having a drill chuck installed at its front end, capable of preventing a purulent matter due to the infection by bacteria from being formed at the region of an orthopedic operation of a patient's body by making an antiseptic cover for completely enclosing the outside of the electric-powered drill, which may be not properly disinfected or sterilized, to be easily installed, and is capable of substantially saving time and labor required to perform an orthopedic medical operation by making a medical pin to be simply and safely inserted into a fractured bone or a dislocated bone of a patient.

Furthermore, the present invention relates to an auxiliary apparatus for inserting a pin into a broken bone, which is capable of largely enhancing the preciseness of an orthopedic medical operation by moveably inserting a position-displaying member for displaying the through direction and the through position of the medical pin into a guide groove that is formed at an outer side surface of the support handle in the longitudinal direction, so that the position-displaying member can slide in the forward and reward direction along the guide groove, and thus by making an operating surgeon easily guess the through direction and the through position of the medical pin with the aid of the position-displaying member mounted to the support handle when the operating surgeon inserts the medical pin into a fractured bone or a dislocated bone of a patient.

2. Description of the Related Art

Generally, at a field of an orthopedic surgery fighting a disease generated at a bone or an articulation of a person, an orthopedist takes a radiograph of a fractured bone or a dislocated bone of a patient by using radioactive rays. As shown in FIG. 1, the orthopedist inserts a medical pin 17, which is conventionally called K-wire, into a bone 18 of a patient's finger and fixes it therein so as to safely maintain a correctional state of the fractured bone or the dislocated bone until the patient completely restores in health.

In order to insert the medical pin 17 into the fractured bone or the dislocated bone of the patient, a manually operated hand drill 20 as shown in FIG. 2 has been widely used in a field of an orthopedic surgery. A drill chuck 25 driven by manually operating a handle 22 is installed at a front end of a body 21 having a handle portion 23. The drill chuck 25 is connected to the body 21 via a connecting shaft 24 extending there between.

If an orthopedist wants to use the conventional manually operated handle drill 20 in order to insert the medical pin 17 into the fractured bone or the dislocated bone of the patient, he or she must insert the medical pin 17 into an interior of the connecting shaft 24 through the drill chuck 25. At this time, the orthopedist tightens the drill chuck 25 by using a chuck key so as to prevent the medical pin 17 from being shaken within the drill chuck 25. Next, the orthopedist makes the front end of the medical pin 17 to be contacted with the distal end of the bone 18 to be cured and thereafter he or she slowly rotates the handle 22 attached to a one side of the body 21 of the hand drill 20. As a result, the connecting shaft 24 and the drill chuck 25 are rotated together. Continuously the medical pin 17 mounted to the drill chuck 25 begins to be rotated and then it is begins to be inserted into the bone 18. Preferably, the medical pin 17 is provided with a drill blade formed at the distal end thereof and thereby it can be easily inserted into the bone 18.

Because the fractured bone or the dislocated bone is located beneath a skin of the patient, it is difficult to ascertain the positional state of them during insertion of the medical pin 17. Accordingly, the orthopedist must have long orthopedic experience and much orthopedic medical operations in the field of an orthopedic surgery in order to precisely insert the medical pin 17 into the center portion of the bone 18 located beneath the skin of the patient.

When the orthopedist inserts the medical pin 17 into the bone 18 by using the conventional manually operated hand drill 20, he or she must grasp the handle portion 23 with his or her one hand and directly rotates the handle 22 attached to the body 21 with his or her other hand. Accordingly, there is one problem that the hand drill 20 may be shaken itself and therefore the medical pin 17 cannot precisely be inserted into a desired position in the bone 18 and thereby it is off the center portion of the bone 18. Consequently, the orthopedic medical operation performed by the orthopedist frequently meets with failure and therefore it must repeatedly perform much new orthopedic medical operations again and again.

When the orthopedist uses the manually operated hand drill 20, he or she must forcibly grasp the handle portion 23 and then slowly rotate the handle 22. Accordingly, this orthopedic medical operation requires a great deal of trouble. Furthermore, since the RPM of the medical pin 17 is much too small, substantial time and labor are necessary for the orthopedist to completely perform the orthopedic medical operation by using the manually operated hand drill 20.

A variety of endeavors for solving these problems have been proposed. One approach, a conventional electric-powered drill, which is widely used in a woodworking art or an industrial purpose, instead of the manually operated hand drill 20, has been proposed. However, one problem associated with this device is that the orthopedist cannot insert a long medical pin 17 into the bone of the patient by using the conventional electric-powered drill because the tool chuck is formed as short for precisely receiving and fixing a drill bit or a screw driver therein. Another problem associated with this device is that an electric motor installed in the conventional electric-powered drill may be damaged due to use of an antiseptic solution while the antiseptic solution is sprayed to the electric-powered drill or may be damaged due to the high temperature and the high pressure while it is sterilized under the high temperature and the high pressure in order to prevent a purulent matter due to the infection by bacteria from being formed at the region of an orthopedic operation of a patient's body

SUMMARY OF THE INVENTION

The present invention solves the foregoing problems. It is one object of the present invention to provide an auxiliary apparatus for inserting a pin into a broken bone, which is capable of being easily mounted to a conventional electric-powered drill, in which a support handle is rotatably mounted onto an outer peripheral surface of a hollow shaft having a drill chuck installed at its front end, capable of preventing a purulent matter due to the infection by bacteria from being formed at the region of an orthopedic operation of a patient's body by making an antiseptic cover for completely enclosing the outside of the electric-powered drill, which may be not properly disinfected or sterilized, to be easily installed, and is capable of substantially saving time and labor required to perform an orthopedic medical operation by making a medical pin to be simply and safely inserted into a fractured bone or a dislocated bone of a patient.

Furthermore, it is another object of the present invention to provide an auxiliary apparatus for inserting a pin into a broken bone, which is capable of largely enhancing the preciseness of an orthopedic medical operation by moveably inserting a position-displaying member for displaying the through direction and the through position of the medical pin into a guide groove that is formed at an outer side surface of the support handle in the longitudinal direction, so that the position-displaying member can slide in the forward and reward direction along the guide groove, and thus by making an operating surgeon easily guess the through direction and the through position of the medical pin with the aid of the position-displaying member mounted to the support handle when the operating surgeon inserts the medical pin into a fractured bone or a dislocated bone of a patient.

In order to achieve the above objects, the present invention provides an auxiliary apparatus for inserting a pin into a broken bone, the auxiliary apparatus comprising:

a shaft including a drill chuck part installed at its outer front end, a handle mounting part disposed at its middle portion, and a tool joint part formed at its rear end, in which a pin inserting hole is formed through an inner side of the shaft, a staged portion and a locking groove are formed at the handle mounting part, and in which a cap bolt is inserted into the tool joint part; and a support handle being rotatably mounted onto the handle mounting part of the shaft, in which a shaft inserting hole is formed through in the support handle, an engaging hole for receiving a release prevention bolt and a joint groove are formed at a radial outer portion of the support handle.

A guide groove is formed at an outer peripheral surface of the supporting handle in the longitudinal direction thereof, in which a position-displaying member is moveably inserted into the guide groove and it can move in the front and reward direction, and in which a front rounded portion having a position-displaying part at its front end is formed at a front end of the position-displaying member and a rear rounded portion having a guide portion at its rear end is formed at a rear end of the position-displaying member.

BRIEF DESCRIPTION OF THE DRAWINGS

The above object and other characteristics and advantages of the present invention will become more apparent by describing in detail a preferred embodiment thereof with reference to the attached drawings, in which.

DETAILED DESCRIPTION OF THE INVENTION

Hereinafter, the auxiliary apparatus for inserting a pin into a broken bone according to the preferred embodiments of the present invention will be explained in more detail with reference to the accompanying drawings.

Figure 1:
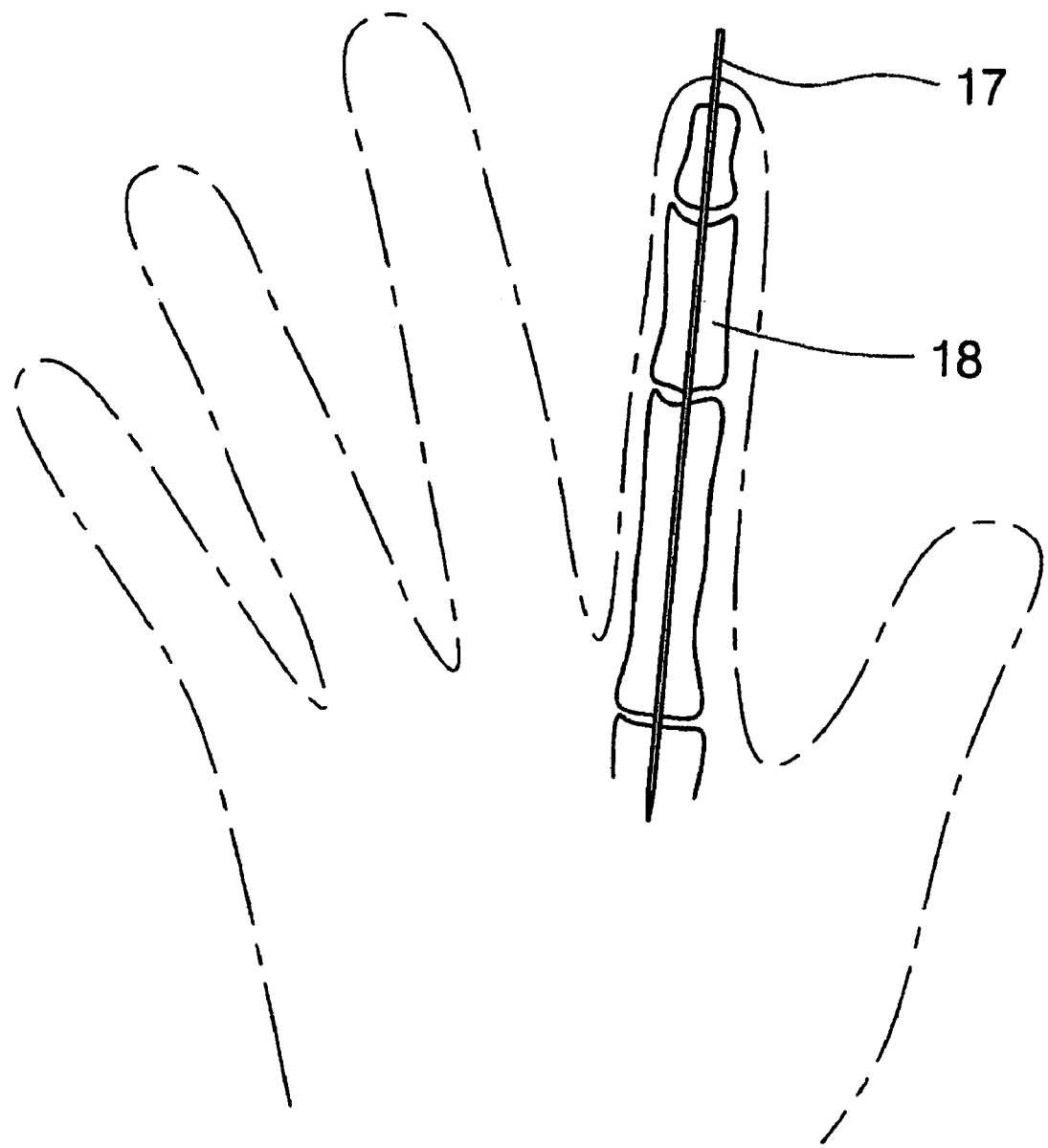
FIG. 1 is a diagrammatical view for showing the medical operational state that a medical pin is inserted into a finger of a patient.
Figure 2:
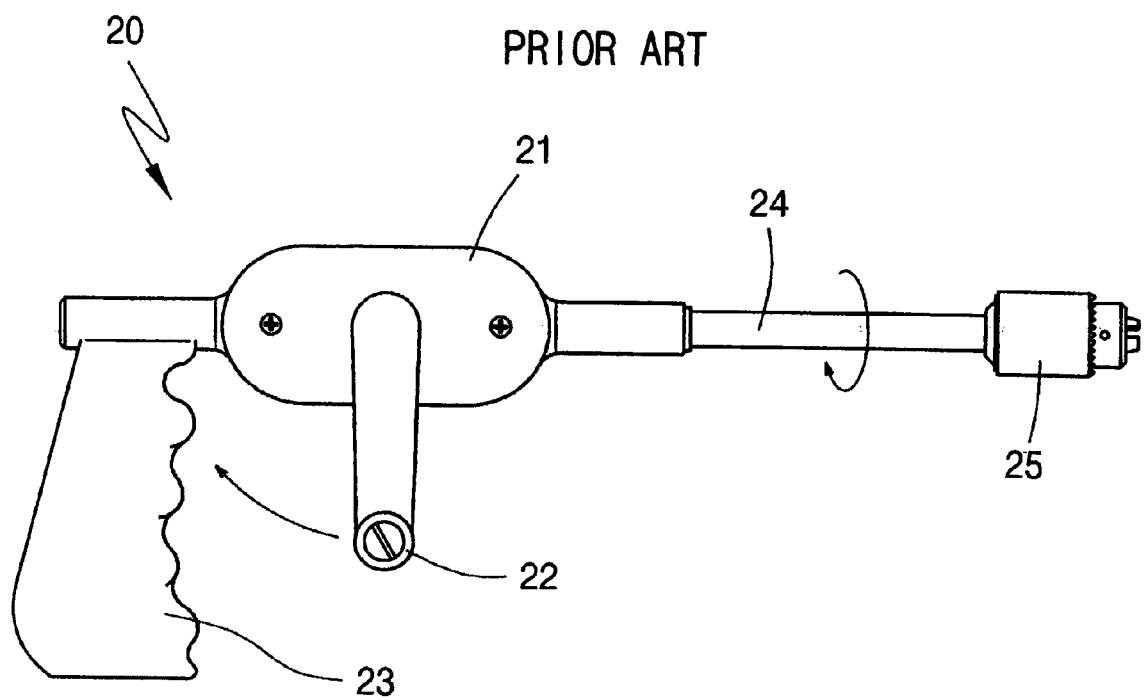
FIG. 2 is a side view of a manually operated hand drill for inserting the medical pin into a patient's broken bone according to a prior art.
Figure 3:
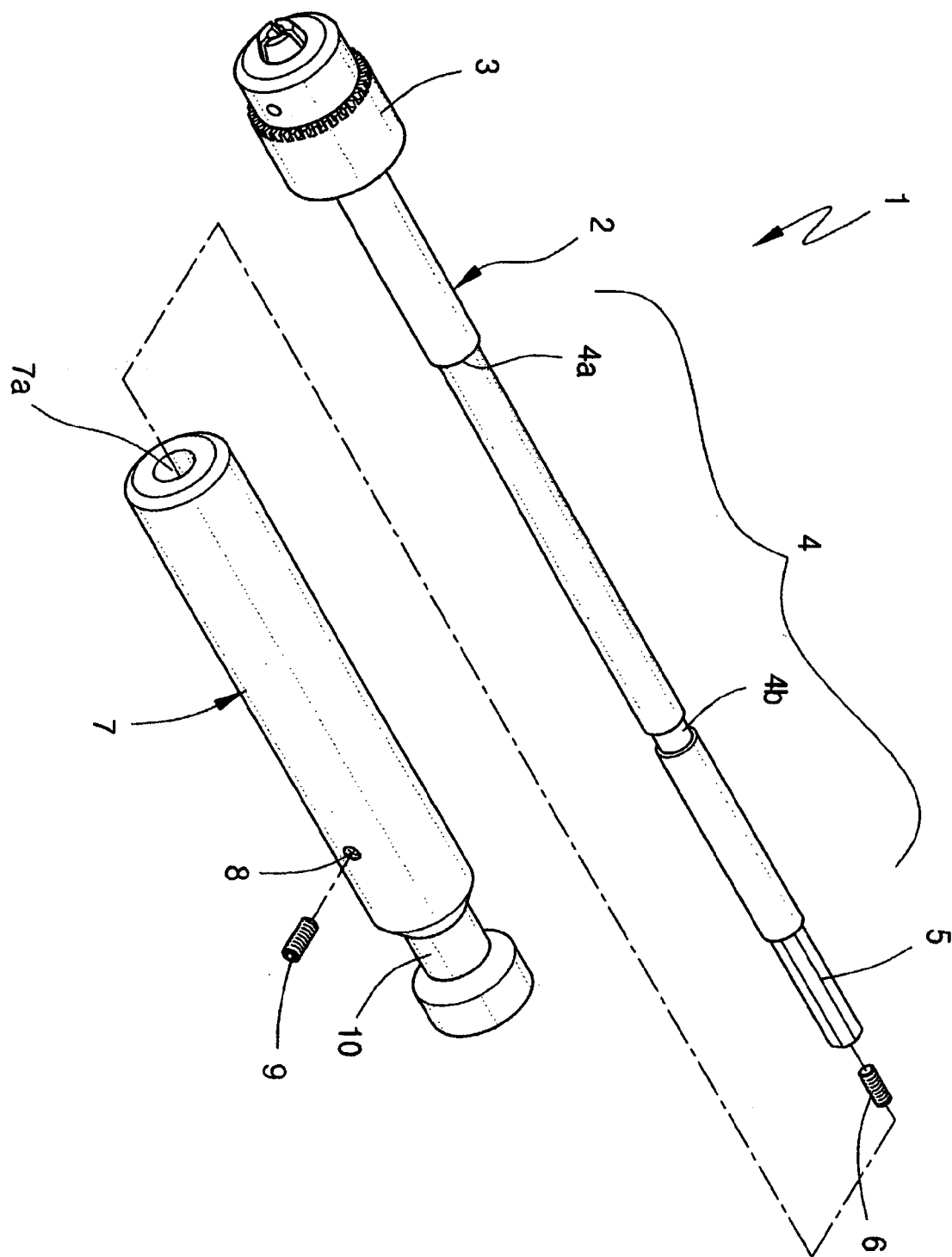
FIG. 3 is an exploded view of an auxiliary apparatus for inserting the medical pin into a broken bone according to a preferred first embodiment of the present invention.
Figure 4:
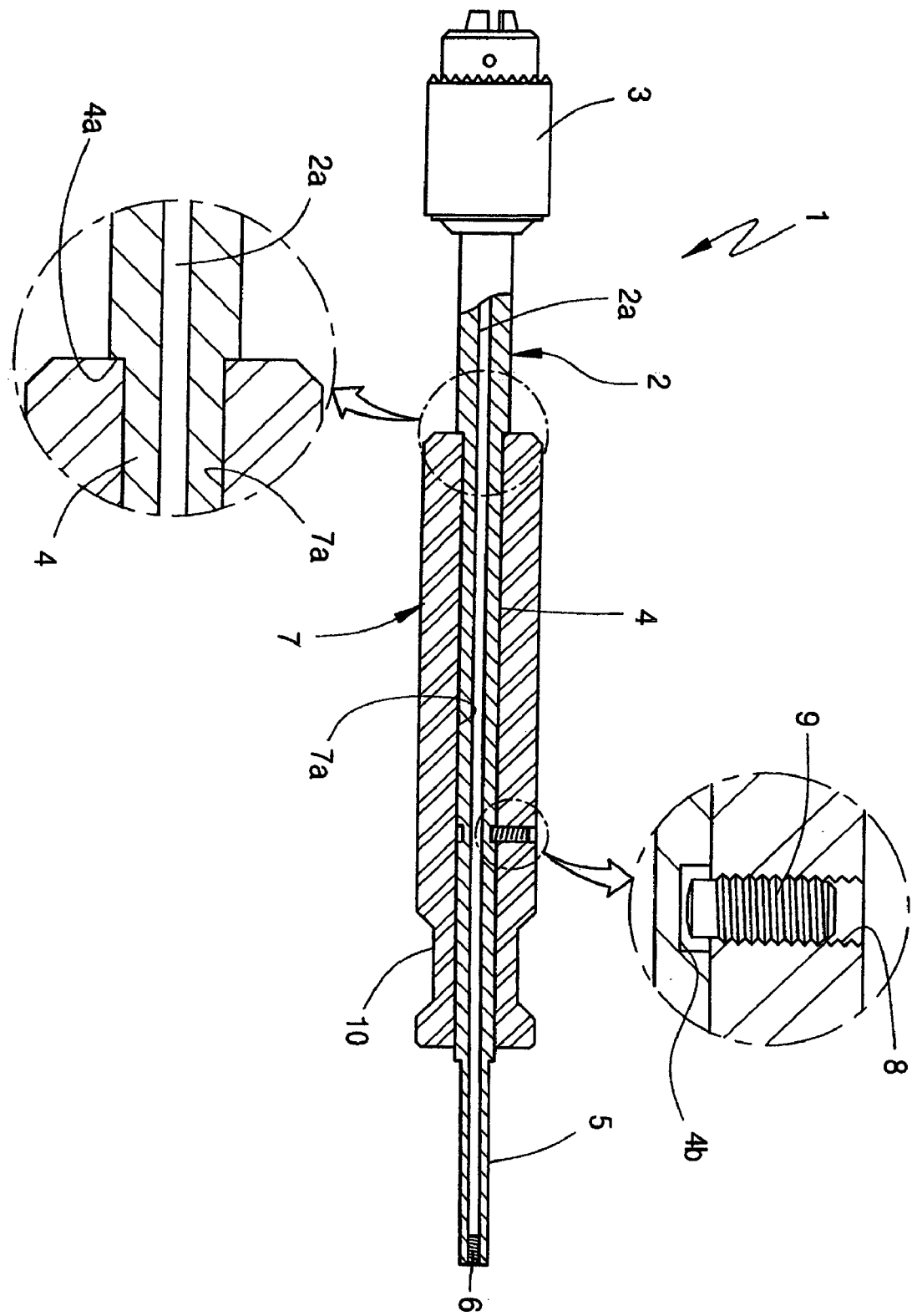
FIG. 4 is a sectional view of the auxiliary apparatus for inserting the medical pin into the broken bone according to the preferred first embodiment of the present invention, for showing the assembled state thereof.
Figure 5:
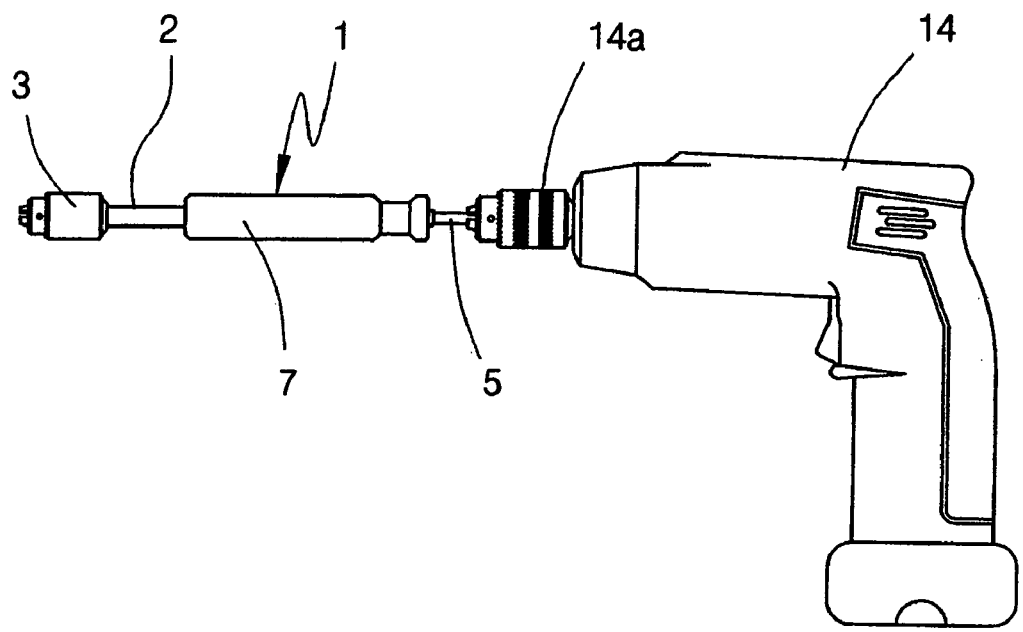
FIGS. 5A and 5B show the use state of the auxiliary apparatus for inserting the medical pin into the broken bone according to the preferred first embodiment of the present invention.
Figure 5:
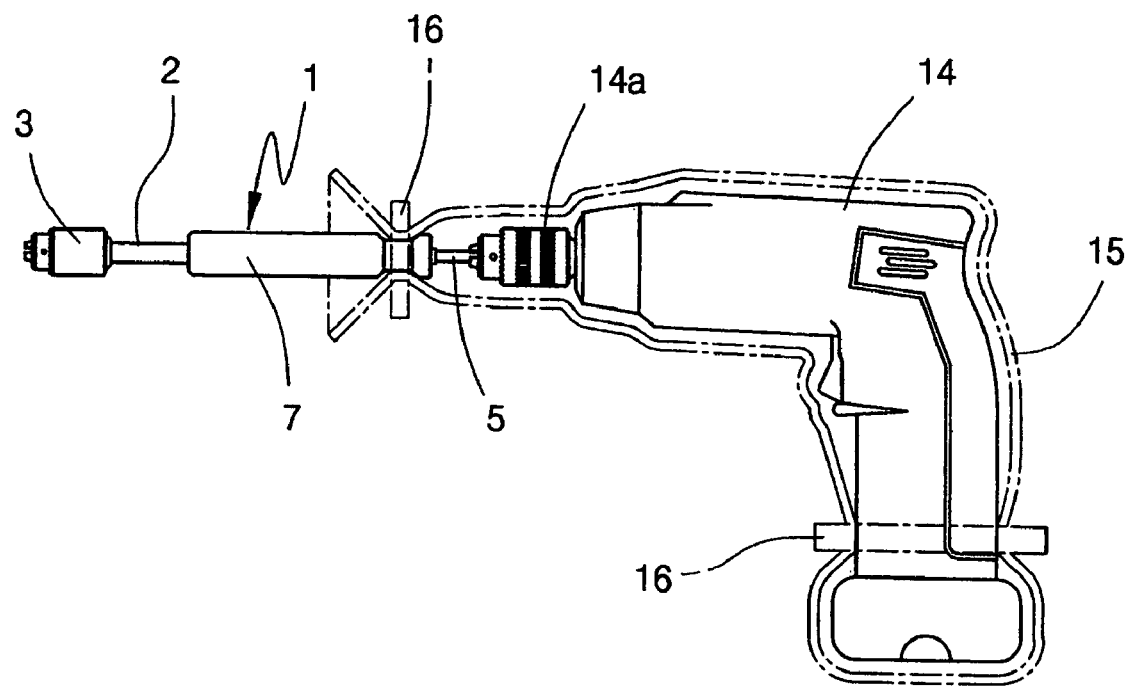

FIG. 3 is an exploded view of an auxiliary apparatus for inserting the medical pin into a broken bone according to a preferred first embodiment of the present invention, FIG. 4 is a sectional view of the auxiliary apparatus for inserting the medical pin into the broken bone according to the preferred first embodiment of the present invention, for showing the assembled state thereof, and FIGS. 5A and 5B show the use state of the auxiliary apparatus for inserting the medical pin into the broken bone according to the preferred first embodiment of the present invention.

As shown in FIGS. 3 and 4, the auxiliary apparatus for inserting the medical pin into the broken bone according to the preferred first embodiment of the present invention comprises a shaft 2 and a support handle 7. A pin inserting hole 2a is formed through an inner side of the shaft 2. A drill chuck part 3 is installed at an outer front end of the shaft 2. A handle mounting part 4 is disposed at a middle portion of the shaft 2, and a tool joint part 5 is formed at a rear end of the shaft 2. At the rear end of the shaft 2, a cap bolt 6 is inserted into the tool joint part 5. A staged portion 4a and a locking groove 4b are formed at the handle mounting part 4. The support handle 7 is rotatably mounted onto the handle mounting part 4 of the shaft 2. A shaft inserting hole 7a is formed through the support handle 7, an engaging hole 8 for receiving a release prevention bolt 9 and a joint groove 10 are formed at a radial outer portion of the support handle 7.

The drill chuck part 3 formed at the front end of the shaft 2 is a conventional drill chuck that is widely used to mount a drill bit or a screw-diver.

As described above, the auxiliary apparatus for inserting the medical pin into the broken bone according to the preferred first embodiment of the present invention can be easily mounted to an electric-powered drill that is widely used in a woodworking art or an industrial purpose. When an orthopedist uses the conventional electric-powered drill employing the auxiliary apparatus for inserting the medical pin into the broken bone according to the present invention in a state that it is mounted to the conventional electric-powered drill, it is required to sterilize the conventional electric-powered drill at the same manner as that of conventional medical instruments so as to prevent a purulent matter due to the infection by bacteria from being formed at the region of an orthopedic operation of a patient's body. However, an electric motor mounted in the electric-powered drill may be damaged due to the use of an antiseptic solution while the antiseptic solution is sprayed to the electric-powered drill or may be damaged due to the high temperature and the high pressure while it is sterilized under the high temperature and the high pressure. Therefore, the electric-powered drill may be sterilized as follows.

First, as shown in FIG. 5A, a tool joint part 5 of the auxiliary apparatus 1 for inserting the medical pin into the broken bone is subjected to a conventional sterilizing process. Then, the tool joint part 5 of the auxiliary apparatus 1 is inserted into a tool chuck 14a of the conventional electric-powered drill 14. Under this state, the tool chuck 14a gets tighten with the aid of a chuck key so as to prevent the auxiliary apparatus 1 from being shaken itself.

Under the state that the auxiliary apparatus 1 for inserting the medical pin into the broken bone is mounted to the tool chuck 14a of the conventional electric-powered drill 14, in order to prevent a purulent matter due to the infection by bacteria from being formed at the region of an orthopedic operation of a patient's body, as shown in FIG. 5B, a pouch-shaped antiseptic cover 15 of which a front end and a rear end are open such as a conventional disinfected bandage completely encloses the electric-powered drill 14 so that the total body of the electric-powered drill 14 is not exposed to the outside.

At this time, the front end a front end of the antiseptic cover 15 is tied by means of a tie band 16 at a joint groove 10 formed at the support handle 7 of the auxiliary apparatus 1 mounted to the tool chuck 14a of the electric-powered drill 14. Likewise, the rear end is tied by means of the tie band 16 at a handle portion of the electric-powered drill 14. Thus, when the orthopedist inserts the medical pin 17 into the broken bone of a patient by using the electric-powered drill 14, the antiseptic cover 15 is not wound around the shaft 2 of the auxiliary apparatus 1 mounted to the tool chuck 14a of the electric-powered drill 14 and thereby it is convenient to use the electric-powered drill 14.

Since an electric motor, which may be easily damaged, is installed in the conventional electric-powered drill 14, it is hard to spray an antiseptic solution toward the electric-powered drill 14 or to sterilize the electric-powered drill 14 under a high temperature and a high pressure. According to the present invention, the electric-powered drill 14 is fully enclosed by the antiseptic cover 15 and then the medical pin 17 is inserted through the drill chuck part 3 into the pin inserting hole 2a of the shaft 2. At this time, a front end of the medical pin 17 slightly protrudes to the outside. After insertion of the medical pin 17, the drill chuck part 3 gets tighten by means of the chuck key. Under this state, the orthopedist grasps the handle of the electric-powered drill 14 with his or her one hand and he or she grasps the support handle 7 of the auxiliary apparatus 1 with his or her other hand. Continuously, the orthopedist makes the front end of the medical pin 17 to be contacted with the distal end of the bone 18 to be cured and thereafter he or she operates the electric-powered drill 14.

The rotational force of the electric-powered drill 14 is transmitted to the shaft 2 of the auxiliary apparatus 1 mounted to the tool chuck 14a of the electric-powered drill 14. The shaft 2 can freely rotate within the support handle 7 due to the rotational force transmitted from the electric-powered drill 14. Also, the medical pin 17, which is inserted into the pin inserting hole 2a of the shaft 2 and is fixed to the drill chuck part 3, rotates together with the shaft 2 in accordance with the rotation of the shaft 2 and continuously it begins to be gradually inserted into the bone.

At this time, when the shaft 2 is rotated, the support handle 7 mounted onto the handle mounting part 4 of the shaft 2 can maintain its standstill regardless of the rotation of the shaft 2. Furthermore, the support handle 7 is not released from the shaft 2 by means of the release prevention bolt 9 that is inserted into an engaging hole 8 of the support handle 7 and then it is locked in the locking groove 4b of the shaft 2. As a result, it is possible to perform the insertion of the medical pin in a state that the orthopedist can stand at a fine posture.

When the orthopedist performs the insertion of the medical pin 17 into the broken bone, a blood introduced through the pin inserting hole 2a of the shaft 2 cannot be introduced into the inside of the electric-powered drill 14 by means of the cap bolt 6 engaged with the tool joint part 5 of the shaft 2. Accordingly, it is possible to prevent the electric-powered drill 14 from being damaged due to introduction of the blood.

After inserting a part of the medical pin 17 into the broken bone at a predetermined depth, the other part of the medical pin 17 is slightly exposed to the outside by releasing the drill chuck part 3 for fixing a medical pin 26. Under this state, the medical pin 17 is fixed by tightening the drill chuck part 3 again. Then, the medical pin 17 is inserted into the broken bone due to operation of the electric-powered drill 14. By repeatedly performing this medical operational process until the distal end of the medical pin 17 is slightly exposed to the outside, the insertion of the medical pin 17 has been completed.

In a state that the fracture of a bone and the dislocation of a bone have been completely cured after the lapse of certain time from the completion of the inserting the medical pin 17, the orthopedist makes the drill chuck part 3 to be engaged and fixed to the distal end of the medical pin 17, which is slightly exposed to the outside. As a result, it is possible to remove the medical pin 17 by rotating and slowly picking up the medical pin 17 during operation of the electric-powered drill 14.

Hereinafter, the auxiliary apparatus for inserting a pin into a broken bone according to a preferred second embodiment of the present invention will be explained in more detail with reference to the accompanying drawings.

Figure 6:
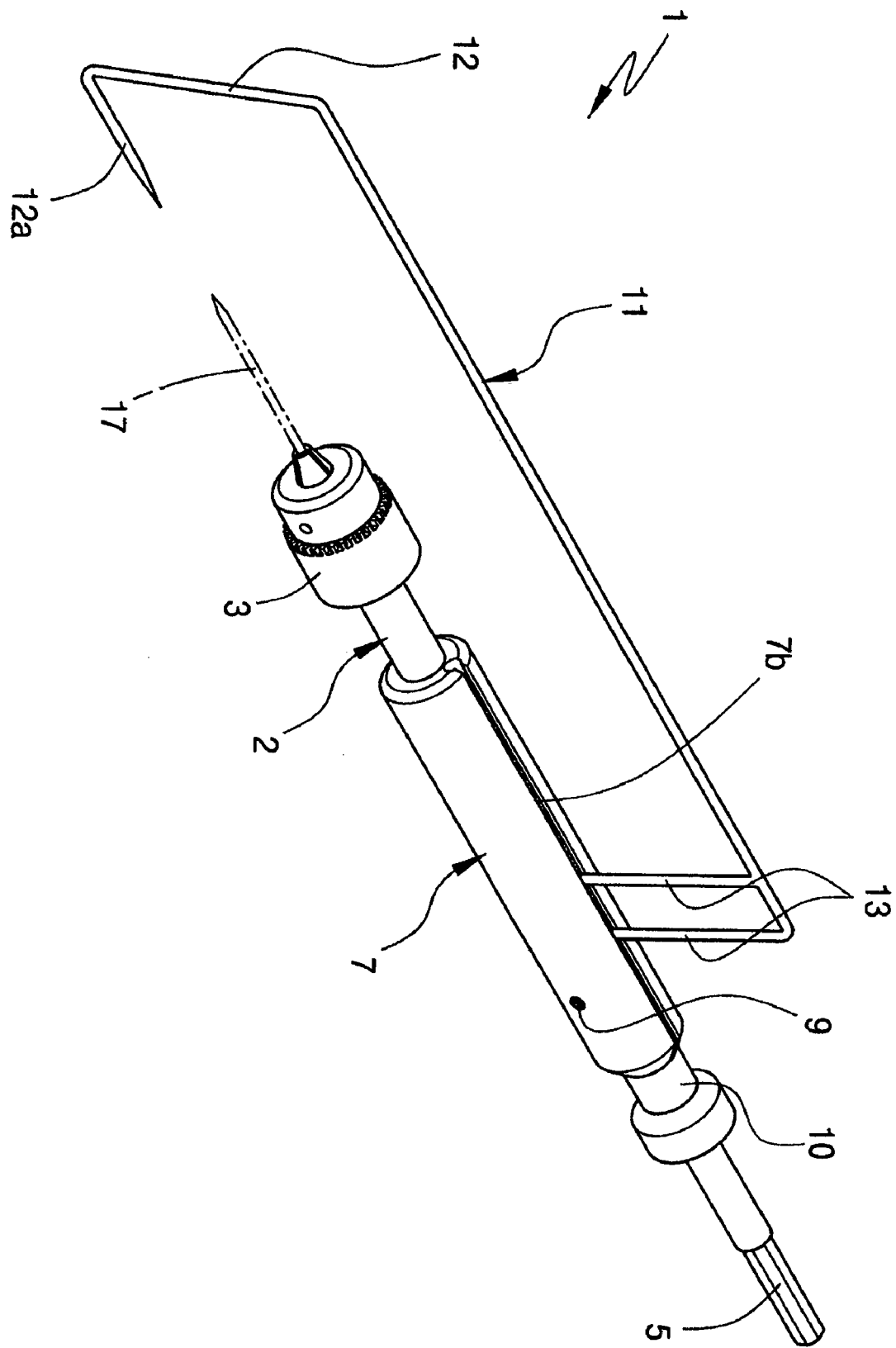
FIG. 6 is a perspective view of an auxiliary apparatus for inserting the medical pin into the broken bone according to a preferred second embodiment of the present invention.
Figure 7:
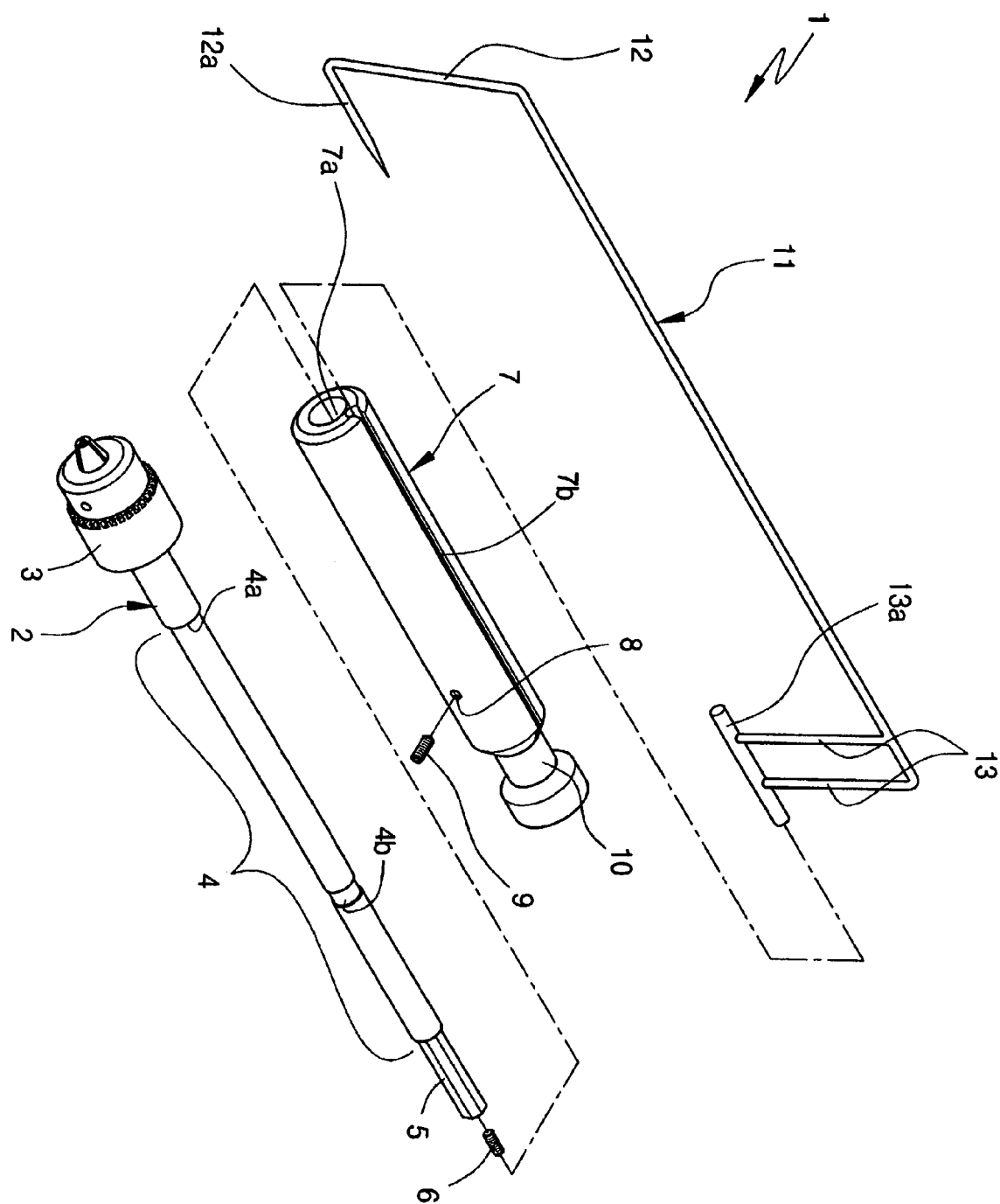
FIG. 7 is an exploded view of the auxiliary apparatus for inserting the medical pin into a broken bone according to the preferred second embodiment of the present invention.
Figure 8:
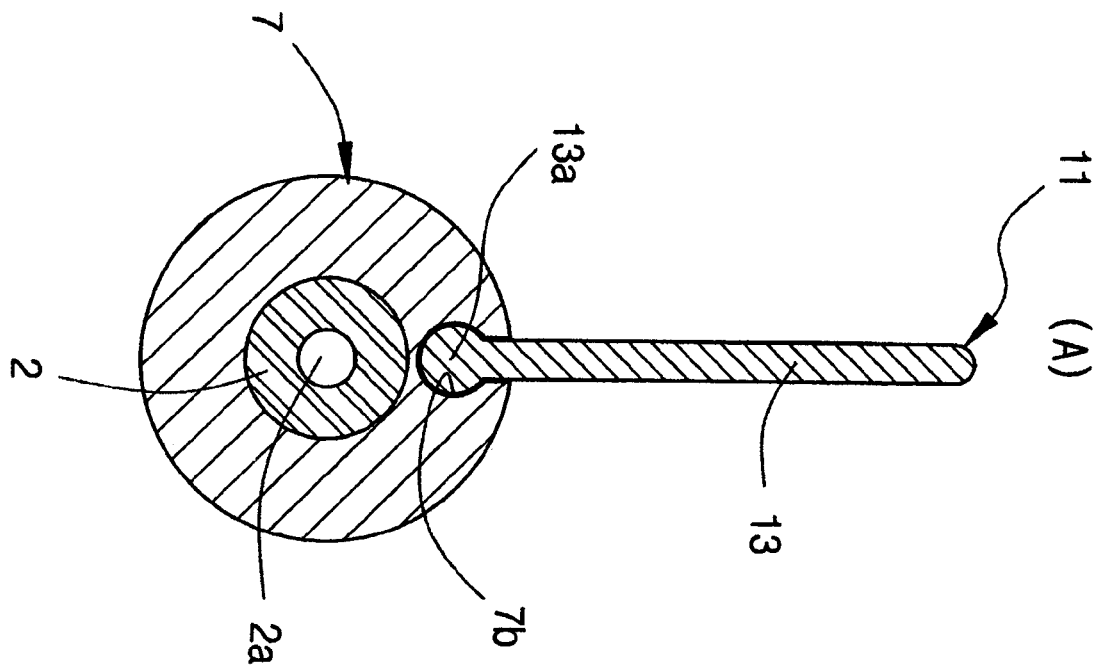
FIGS. 8A and 8B are front sectional views for showing the state that a position-displaying member is assembled with a support handle according to the preferred first embodiment of the present invention.
Figure 8:
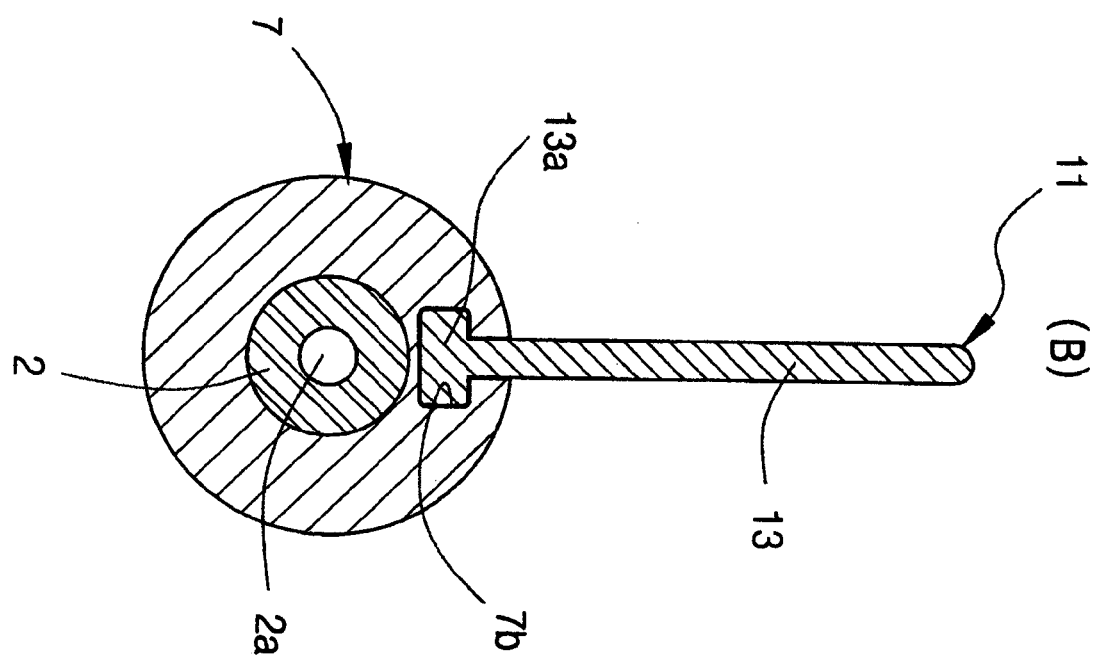

FIG. 6 is a perspective view of an auxiliary apparatus for inserting the medical pin into the broken bone according to a preferred second embodiment of the present invention, FIG. 7 is an exploded view of the auxiliary apparatus for inserting the medical pin into a broken bone according to the preferred second embodiment of the present invention, FIGS. 8A and 8B are front sectional views for showing the state that a position-displaying member is assembled with a support handle according to the preferred first embodiment of the present invention, and FIGS. 9A to 9D show the use state of the auxiliary apparatus for inserting the medical pin into the broken bone according to the preferred second embodiment of the present invention.

As shown in FIGS. 6 and 7, in the auxiliary apparatus for inserting the medical pin into the broken bone according to the preferred second embodiment of the present invention, a pin inserting hole 2a is formed through an inner side of the shaft 2. A drill chuck part 3 is installed at an outer front end of the shaft 2. A handle mounting part 4 is disposed at a middle portion of the shaft 2, and a tool joint part 5 is formed at a rear end of the shaft 2. The cap bolt 6 is inserted into the tool joint part 5. A staged portion 4a and a locking groove 4b are formed at the handle mounting part 4. The support handle 7 is rotatably mounted onto the handle mounting part 4 of the shaft 2. A shaft inserting hole 7a is formed through in the support handle 7, an engaging hole 8 for receiving the release prevention bolt 9 and a joint groove 10 are formed at a radial outer portion of the support handle 7.

The important technical features of the apparatus for inserting the medical pin into the broken bone according to the preferred second embodiment of the present invention are that a guide groove 7b is formed at an outer peripheral surface of the support handle 7 in the longitudinal direction and a position-displaying member 11 is slideably inserted into the guide groove 7b. At this time, the position-displaying member 11 has a front rounded portion 12 having a position-displaying part 12a at its front end and a rear rounded portion 13 having a guide portion 13a at its rear end. The position-displaying member 11 can slide within the guide groove 7b in the forward direction and the rearward direction.

As shown in FIG. 7, the position-displaying member 11 is installed in the guide groove 7b by inserting the guide portion 13a disposed at the rear rounded portion 13 into the guide groove 7b formed at an outer one side surface of the support handle 7, which is mounted onto the outer peripheral surface of the shaft 2. Preferably, the sectional shape of the guide groove 7b formed in the support handle 7 is correspond to that of the guide portion 13a of the position-displaying member 11 so that the guide portion 13a can freely slide within the guide groove 7b with maintaining the strong engagement there between. Preferably, the sectional shapes of the guide groove 7b and the guide portion 13a are a circular shape or a quadrilateral shape as shown in FIGS. 8A and 8B.

As shown in FIG. 6, since the position-displaying part 12a formed at the front rounded portion 12 is located on an extending line of the medical pin 17 mounted to the drill chuck part 3, the position-displaying member 11 can precisely illustrate the through direction and the through position of the medical pin 17.

At the same manner as that of the preferred first embodiment of the present invention, the auxiliary apparatus for inserting a pin into a broken bone according to the preferred second embodiment of the present invention may be easily mounted to the tool chuck 14a of the electric-powered drill 14, which is widely used in a woodworking art or an industrial purpose.

The auxiliary apparatus 1 including the position-displaying member 11 is subjected to a conventional sterilizing process prior to use in order to prevent a purulent matter due to the infection by bacteria from being formed at the region of an orthopedic operation of a patient's body during the use of the auxiliary apparatus 1. If it is hard to sterilize the electric-powered drill 14 by using the conventional sterilizing process, the electric-powered drill 14 must be completely enclosed by the pouch-shaped antiseptic cover 15 of which a front end and a rear end are open such as a conventional disinfected bandage so that the total body of the electric-powered drill 14 is not exposed to the outside.

Figure 9:
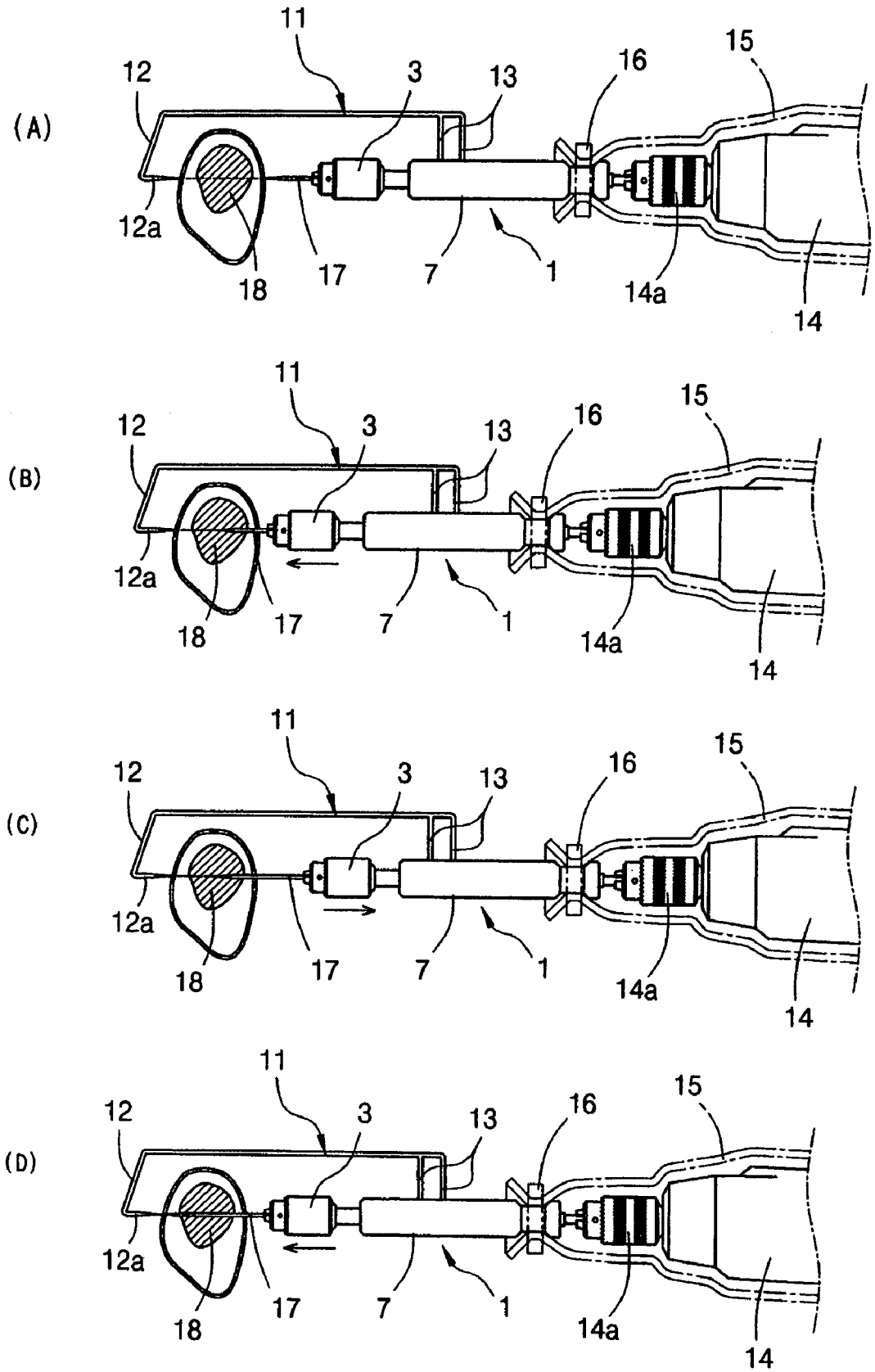
FIGS. 9A to 9D show the use state of the auxiliary apparatus for inserting the medical pin into the broken bone according to the preferred second embodiment of the present invention.

Herein after, the medical operational process for inserting the medical pin 17 into a broken bone by using the auxiliary apparatus according to the preferred second embodiment of the present invention will be explained in more detail with reference to FIG. 9.

If an orthopedist wants to use the auxiliary apparatus for inserting a pin into a broken bone according to the preferred second embodiment of the present invention in order to insert the medical pin 17 into the fractured bone or the dislocated bone of the patient, he or she must insert the long medical pin 17 into an interior of the drill chuck part 3 of the auxiliary apparatus 1 mounted to the tool chuck 14a of the electric-powered drill 14, as shown in FIG. 9A. Thereafter, the orthopedist properly controls a gap between the distal end of the medical pin 17 and the distal end of the position-displaying part 12a of the position-displaying member 11 by moving the position-displaying member 11 mounted to the support handle 7 of the auxiliary apparatus 1 in the forward and reward directions in accordance with the diameter and the length of the diseased part to be cured. Then, the orthopedist makes the distal end of the medical pin 17 and the distal end of the position-displaying part 12a to be contacted with the both sides of the diseased part of the patient. Accordingly, the orthopedist can easily ascertain the through direction and the through position of the medical pin 17 to be inserted into the bone, which is to be cured, due to operation of the position-displaying member 11 with naked eyes.

After ascertaining the through direction and the through position of the medical pin 17 to be inserted into the bone, which those are illustrated by the position-displaying member 11, the orthopedist grasps the handle of the electric-powered drill 14 with his or her one hand and he or she grasps the support handle 7 of the auxiliary apparatus 1, in which the medical pin 17 is mounted thereto with safe, with his or her other hand.

Under the state that the orthopedist grasps the auxiliary apparatus 1 with safe, as shown in FIG. 9B, the orthopedist operates the electric-powered drill and then makes it to be slowly moved toward the bone 18. Then, the auxiliary apparatus 1 mounted to the tool chuck 14a of the electric-powered drill 14 slowly moves forward. Alternatively, the position-displaying member 11 mounted to the support handle 7 of the auxiliary apparatus 1 moves backward due to the force for pulling the rear rounded portion 13 of the position-displaying member 11 with a finger of the hand grasping the support handle 7.

The contact between the position-displaying part 12a of the position-displaying member 11 and the diseased part of the patient to be cured is continuously maintained by pulling the rear rounded portion 13 of the position-displaying member 11 mounted to the support handle 7 with the aid of partial fingers of the hand grasping the support handle 7 until the medical pin 17 is completely inserted. Accordingly, it is possible to easily forecast the through direction and the through position of the medical pin 17 due to the operation of the position-displaying part 12a of the position-displaying member 11 during insertion of the medical pin 17. Consequently, it is possible to precisely and safely insert the medical pin 17 into the bone 18 to be cured.

Furthermore, since the medical pin 17 has a substantially long length, it may be inserted into the bone 18 at a predetermined depth. After inserting the medical pin 17 into the bone 18, as shown in FIG. 9C, the orthopedist makes the drill chuck part 3 to be released by using a chuck key and thereby a part of the medical pin 17 inserted into the pin inserting hole 2a of the shaft 2 is slightly exposed to the outside. Under this state, the orthopedist tightens the drill chuck part 3 again so as to fix the medical pin 17. As shown in FIG. 9D, the orthopedist inserts the drawn out medical pin 17 into the bone 18 again at a predetermined length that is correspond to the length of the drawn out medical pin 17. This process is repeatedly performed by the orthopedist and the orthopedist can insert the medical pin 17 into the bone with safe by precisely forecasting the through direction and the through position of the medical pin 17 due to operation of the position-displaying member 11.

As described above, the auxiliary apparatus for inserting a pin into a broken bone according to the present invention is capable of being easily mounted to a conventional electric-powered drill, in which a support handle is rotatably inserted into an outer peripheral surface of a hollow shaft having a drill chuck installed at its front end, capable of preventing a purulent matter due to the infection by bacteria from being formed at the region of an orthopedic operation of a patient's body by making an antiseptic cover for completely enclosing the outside of the electric-powered drill, which may be not properly disinfected or sterilized, to be easily installed, capable of substantially saving time and labor required to perform an orthopedic medical operation by making a medical pin to be simply and safely inserted into a fractured bone or a dislocated bone of a patient, and is capable of easily and safely performing an orthopedic operation by employing the auxiliary apparatus at the medical operation for inserting the medical pin, at a variety of drilling works in field of the orthopedic surgery or at a variety of screw fixing works for fixing various supporting members to a fractured bone or a dislocated bone of a patient.

Furthermore, the auxiliary apparatus for inserting a pin into a broken bone according to the present invention is capable of largely enhancing the preciseness of an orthopedic medical operation by moveably inserting a position-displaying member for displaying the through direction and the through position of the medical pin into a guide groove that is formed at an outer side surface of the support handle in the longitudinal direction, so that the position-displaying member can slide in the forward and reward direction along the guide groove, and thus by making an operating surgeon easily guess the through direction and the through position of the medical pin with the aid of the position-displaying member mounted to the support handle when the operating surgeon inserts the medical pin into a fractured bone or a dislocated bone of a patient. Furthermore, this auxiliary apparatus can be used for various drilling works performed at the orthopedic surgery and can easily provide the operating surgeon with a proceeding direction and a through direction and a through position of the drill due to operation of the position-displaying member 11 mounted to the support handle. Consequently, it is possible to largely enhance the preciseness of the orthopedic medical operation.

While the present invention has been particularly shown and described with reference to the particular embodiments thereof, it will be understood by those skilled in the art that various changes in form and details may be effected therein without departing from the spirit and scope of the invention as defined by the appended claims.

What is claimed is:

1. An auxiliary apparatus for inserting a pin into a broken bone, the auxiliary apparatus comprising:
   a shaft including a drill chuck part installed at its outer front end, a handle mounting part disposed at its middle portion, and a tool joint part formed at its rear end, in which a pin inserting hole is formed through an inner side of the shaft, a staged portion and a locking groove are formed at the handle mounting part, and in which a cap bolt is inserted into the tool joint part; and
   a support handle being rotatably mounted onto the handle mounting part of the shaft, in which a shaft inserting hole is formed through in the support handle, an engaging hole for receiving a release prevention bolt and a joint groove are formed at a radial outer side of the support handle;
   wherein a guide groove is formed at an outer peripheral surface of the supporting handle in the longitudinal direction thereof, in which a position-displaying member is moveably inserted into the guide groove and it can move within the guide groove in the front and rearward direction, and in which a front rounded portion having a position-displaying part at its front end is formed at a front end of the position-displaying member and a rear rounded portion having a guide portion at its rear end is formed at a rear end of the position-displaying member.

* * * * *